(12) United States Patent
Pailliotet

(10) Patent No.: US 6,556,298 B1
(45) Date of Patent: Apr. 29, 2003

(54) METHOD AND SYSTEM FOR NON-DESTRUCTIVE DYE PENETRATION TESTING OF A SURFACE

(75) Inventor: Pierre-Marie Pailliotet, Soisy sur Seine (FR)

(73) Assignee: Holores, Inc., Port St. Luae, FL (US)

( * ) Notice: Subject to any disclaimer, the term of this patent is extended or adjusted under 35 U.S.C. 154(b) by 0 days.

(21) Appl. No.: 09/647,419

(22) PCT Filed: Apr. 5, 1999

(86) PCT No.: PCT/FR99/01942
§ 371 (c)(1),
(2), (4) Date: Sep. 29, 2000

(87) PCT Pub. No.: WO00/08449
PCT Pub. Date: Feb. 17, 2000

(30) Foreign Application Priority Data
Aug. 5, 1998 (FR) .............................. 98 10062

(51) Int. Cl.⁷ .............................. G01J 4/00; G01J 1/58; G01N 21/00; G21G 5/00
(52) U.S. Cl. ................ 356/369; 356/237.2; 250/458.1; 250/492.1
(58) Field of Search .............................. 356/369, 237.2, 356/71; 250/302, 458.1, 461.1, 492.2, 492.1

(56) References Cited

U.S. PATENT DOCUMENTS

| | | | | |
|---|---|---|---|---|
| 3,774,030 A | * | 11/1973 | O'Connor et al. | 250/302 |
| 4,418,315 A | * | 11/1983 | Edwards et al. | 324/202 |
| 4,508,450 A | * | 4/1985 | Ohshima et al. | 250/559.45 |
| 4,598,997 A | * | 7/1986 | Steigmeier et al. | 250/559.41 |
| 4,621,193 A | * | 11/1986 | Van Hoye | 250/302 |
| 4,641,518 A | * | 2/1987 | Hutchings | 250/302 |
| 4,699,512 A | | 10/1987 | Koshi | |
| 4,755,752 A | * | 7/1988 | Fitzpatrick | 324/200 |
| 4,821,117 A | * | 4/1989 | Sekiguchi | 348/68 |
| 4,893,008 A | | 1/1990 | Horikawa | |
| 5,115,136 A | * | 5/1992 | Tomasch | 250/302 |
| 5,133,198 A | | 7/1992 | Bachmann | |
| 5,150,175 A | * | 9/1992 | Whitman et al. | 250/559.29 |
| 5,333,052 A | | 7/1994 | Finarov | |
| 5,539,514 A | * | 7/1996 | Shishido et al. | 356/237.4 |
| 5,554,318 A | | 9/1996 | Neumann et al. | |
| 5,701,903 A | * | 12/1997 | Sano et al. | 348/49 |
| 5,790,251 A | * | 8/1998 | Hagiwara | 356/237.1 |
| 5,835,220 A | * | 11/1998 | Kazama et al. | 356/237.2 |
| 5,936,726 A | * | 8/1999 | Takeda et al. | 356/237.2 |
| 5,963,314 A | * | 10/1999 | Worster et al. | 250/559.39 |
| 6,084,716 A | * | 7/2000 | Sanada et al. | 356/237.5 |

* cited by examiner

*Primary Examiner*—Richard A. Rosenberger
*Assistant Examiner*—Gordon J Stock, Jr.
(74) *Attorney, Agent, or Firm*—Blakely Sokoloff Taylor & Zafman

(57) ABSTRACT

A method is presented for non-destructive testing of the state of a surface that may have cracks in it by observing waves emitted by a dye applied to the surface and present in the cracks in response to an incident excitation beam of wavelength appropriate to the dye. The incident excitation beam is an ultraviolet light. The beam is made of rectilinear polarized waves. Waves emitted by the dye are observed through a rotatable polarized wave analyzer. The analyzer is rotated first to eliminate from observation the wave due to the residual dye on the surface and thereafter to determine the depths of the cracks.

14 Claims, 5 Drawing Sheets

METHOD AND SYSTEM FOR NON-DESTRUCTIVE DYE PENETRATION TESTING OF A SURFACE

BACKGROUND OF THE INVENTION

1. Field of the Invention

The invention relates to techniques for non-destructive dye penetration testing of the state of a surface, such as the dye penetration and magnetoscopic techniques in particular.

Non-destructive dye penetration testing, which is used in particular for checking for the presence of cracks in a surface, entails the application to that surface of a dye under conditions enabling the dye to penetrate into the defects to be detected, illuminating the surface with incident light, and observing the light emitted by the dye present in the cracks and by the residual dye on the surface.

The surface is illuminated by a beam from a mercury vapor lamp, for example, or from a neon tube, and which includes radiation capable of exciting the dye, which responds by emitting visible monochromatic light that can be observed by means of a photosensitive system, for example, possibly associated with means for producing a digital image that is then processed by an image processing system.

The color of the visible light depends on the dye used. It is orange, for example, if the dye is rhodamine 6G.

2. Description of Related Art

A technique of the above kind is described in the publication FR 2 711 426, for example.

The problem arises of optimizing the observation, in particular optimizing the observation of cracks, which is disturbed by the simultaneous observation of an image of residual traces of dye which remain on the surface.

One proposal for optimizing the observation involves processing the digital image, for example as described in the aforementioned publication.

Another problem is determining the depth of the cracks.

The publication FR 2 736 152 describes a method and a dye penetration system for determining the dimensions of defects.

The above two publications indicate the difficulty and the consequential complexity of methods and systems that have been designed to optimize the images and to assess the dimensions of cracks.

BRIEF SUMMARY OF THE INVENTION

The present invention provides a method and a system which are remarkably simple, which optimize the images and which assess the depth of the cracks.

The invention is based on the observation that when the dye is excited by a rectilinear polarized wave the dye in an area of the surface or in a crack emits a rectilinear polarized wave at an angle to the incident rectilinear polarized wave which depends on the thickness of the product in the area or the crack concerned.

The invention uses the angle between the incident rectilinear polarized wave and the rectilinear polarized wave emitted by the dye to eliminate from the observation areas where residual dye is present on the surface and retain only areas in which the dye has penetrated into the cracks. This approach is based on the fact that the angle corresponding to a wave reflected by residual dye on the surface is different from that corresponding to the dye present in a crack because the thickness of the residual dye on the surface is always less than the thickness of dye in a crack.

According to another aspect of the invention, the angles corresponding to the cracks are used to determine the depths of the cracks.

A system for implementing the invention therefore includes means for producing a rectilinear polarized incident wave at a wavelength chosen to excite the dye, transmission means for guiding the wave toward the surface to be studied, observation means for observing rectilinear polarized waves emitted by dye on the surface and in the cracks, and means on the path of the emitted waves, between the surface and the observation means, for selecting emitted waves according to the angle between the incident rectilinear polarized wave and the rectilinear polarized wave emitted by the dye.

The surface under examination is illuminated with a rectilinear polarized wave from a non-polarized light source associated with a polarizer or preferably from a polarized light source.

This applies in particular to a laser, which delivers a rectilinear polarized wave with parallel edges.

The laser has the further advantage of emitting perfectly monochromatic light in a very fine beam which is coherent over great distances.

Rectilinear polarized waves emitted by the dye are selected by one or more polarized wave analyzers on the path of the waves.

BRIEF DESCRIPTION OF THE DRAWINGS

Embodiments of the invention are described hereinafter with reference to the figures of the accompanying drawings, in which.

DETAILED DESCRIPTION OF THE INVENTION

The systems implementing the invention shown in the figures include:

a laser (1), transmission means (T) for transmitting the beam from the laser to a surface (S) to be studied or to a calibration surface, and an observation video camera (2) equipped with a telephoto lens and an analyzer (3).

The laser (1) preferably emits polarized ultraviolet light centered on a wavelength appropriate to the dye used, for example a wavelength of 330 nanometers.

Figure 1:
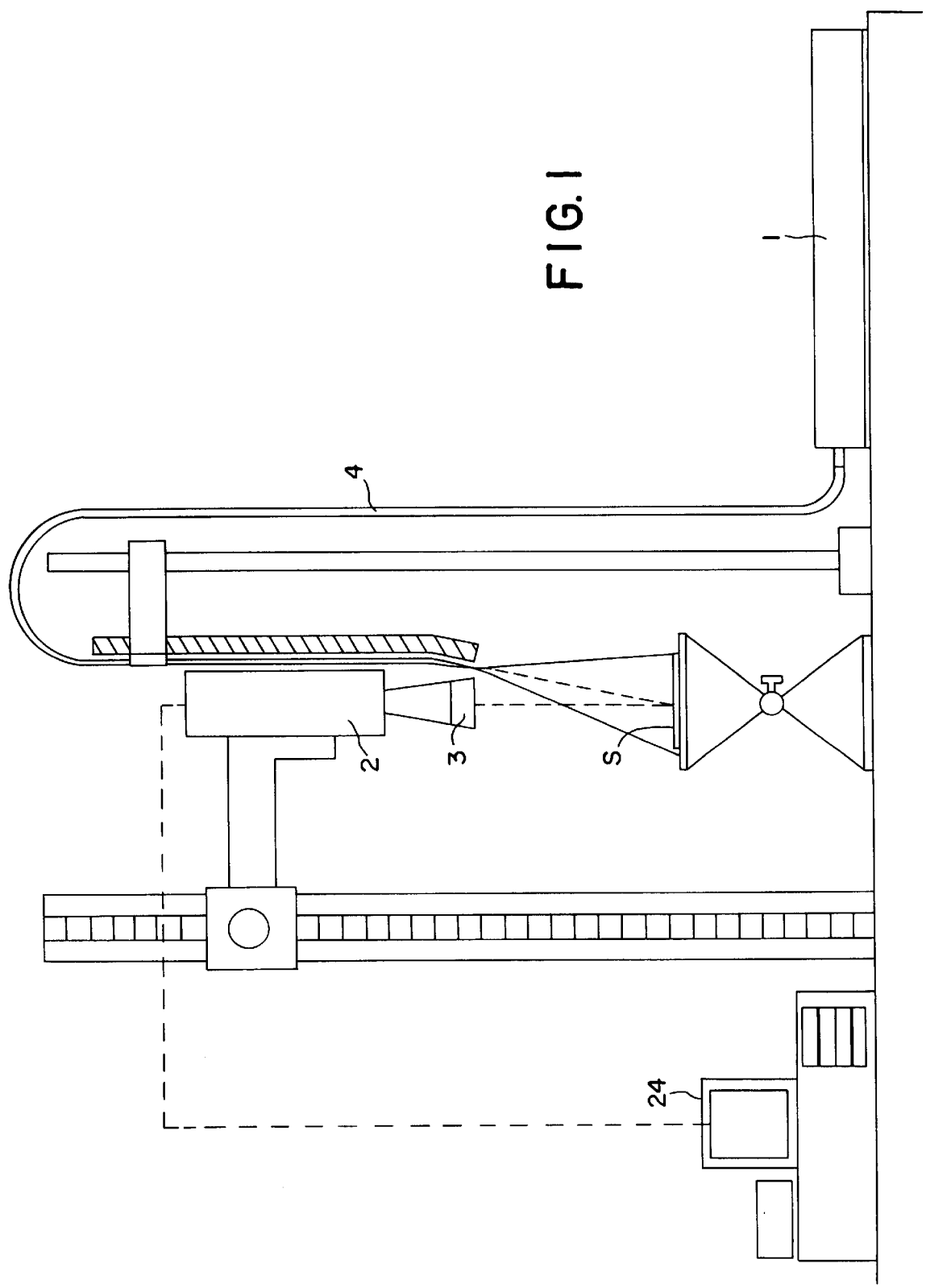
FIG. 1 is a diagram of a first embodiment of a system according to the invention applied to a dye penetration technique for observing cracks in a surface.
Figure 2:
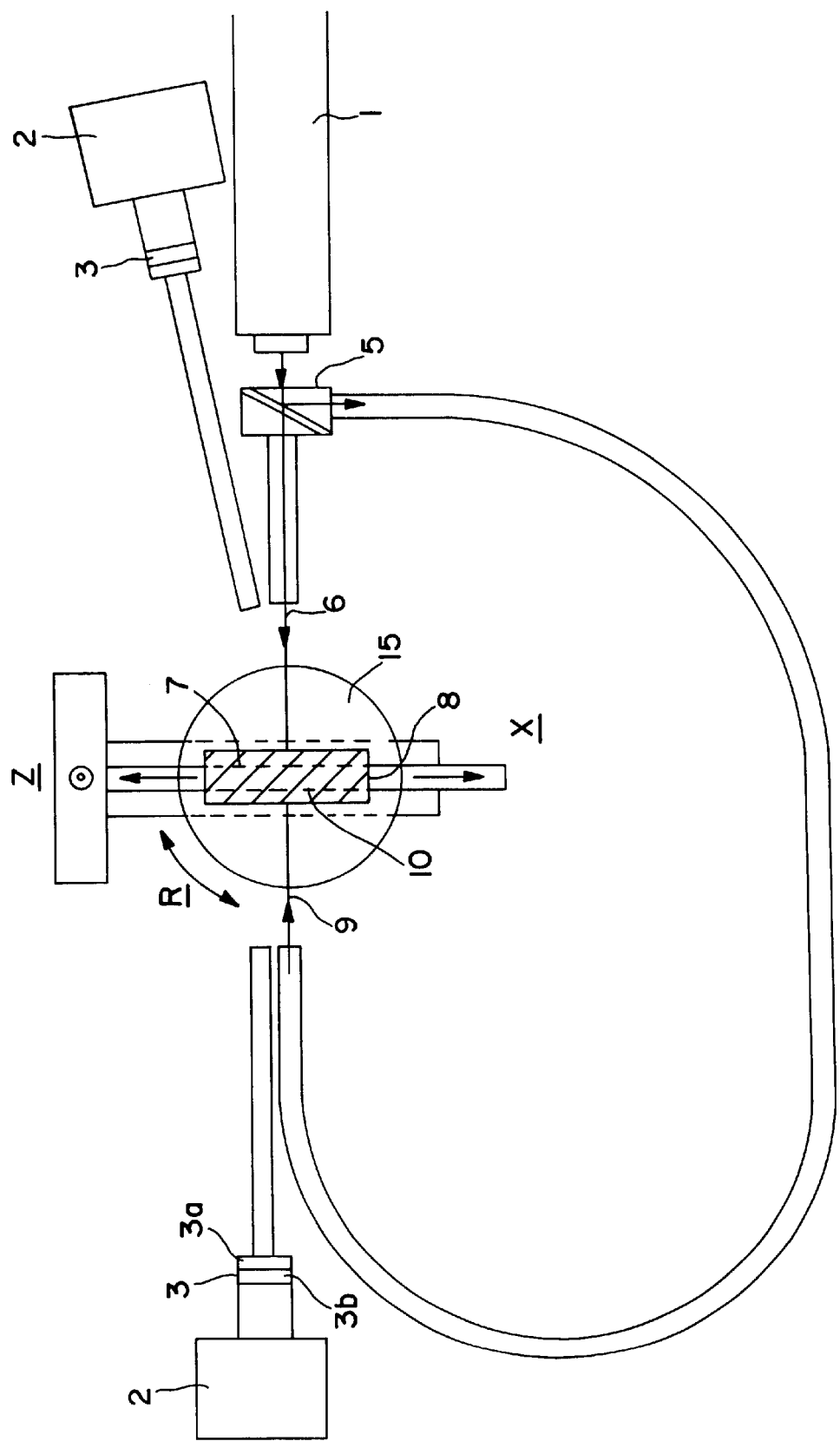
FIG. 2 is a diagram of a second embodiment using a dye penetration technique for simultaneously observing two opposite faces of a part which can rotate and move along X, Y and Z axes.
Figure 3:
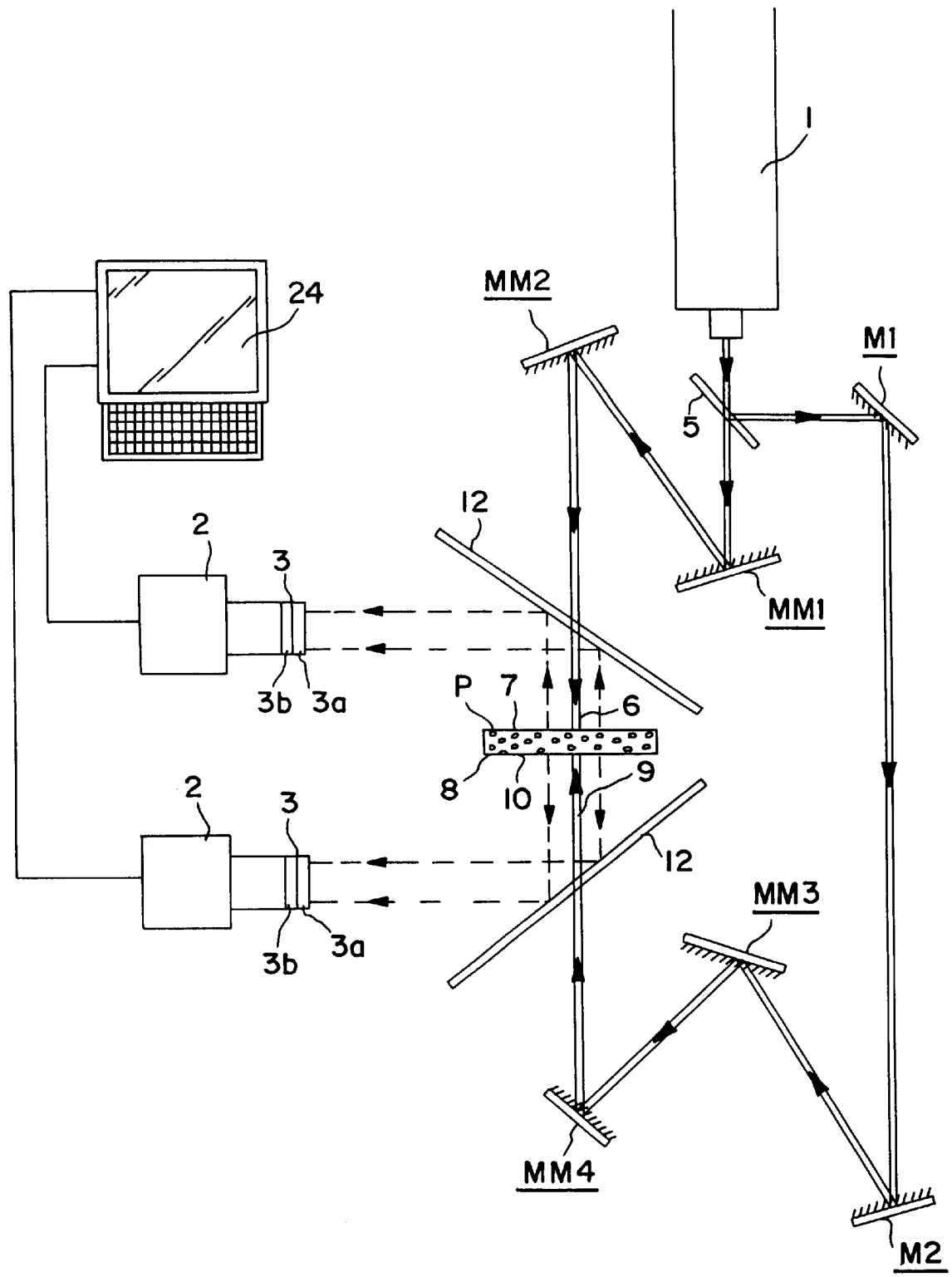
FIG. 3 is a diagram of a third embodiment using a dye penetration technique for simultaneously observing two opposite faces of a plate and including a set of oscillating mirrors which are controlled to scan the incident beam over the faces observed.
Figure 4:
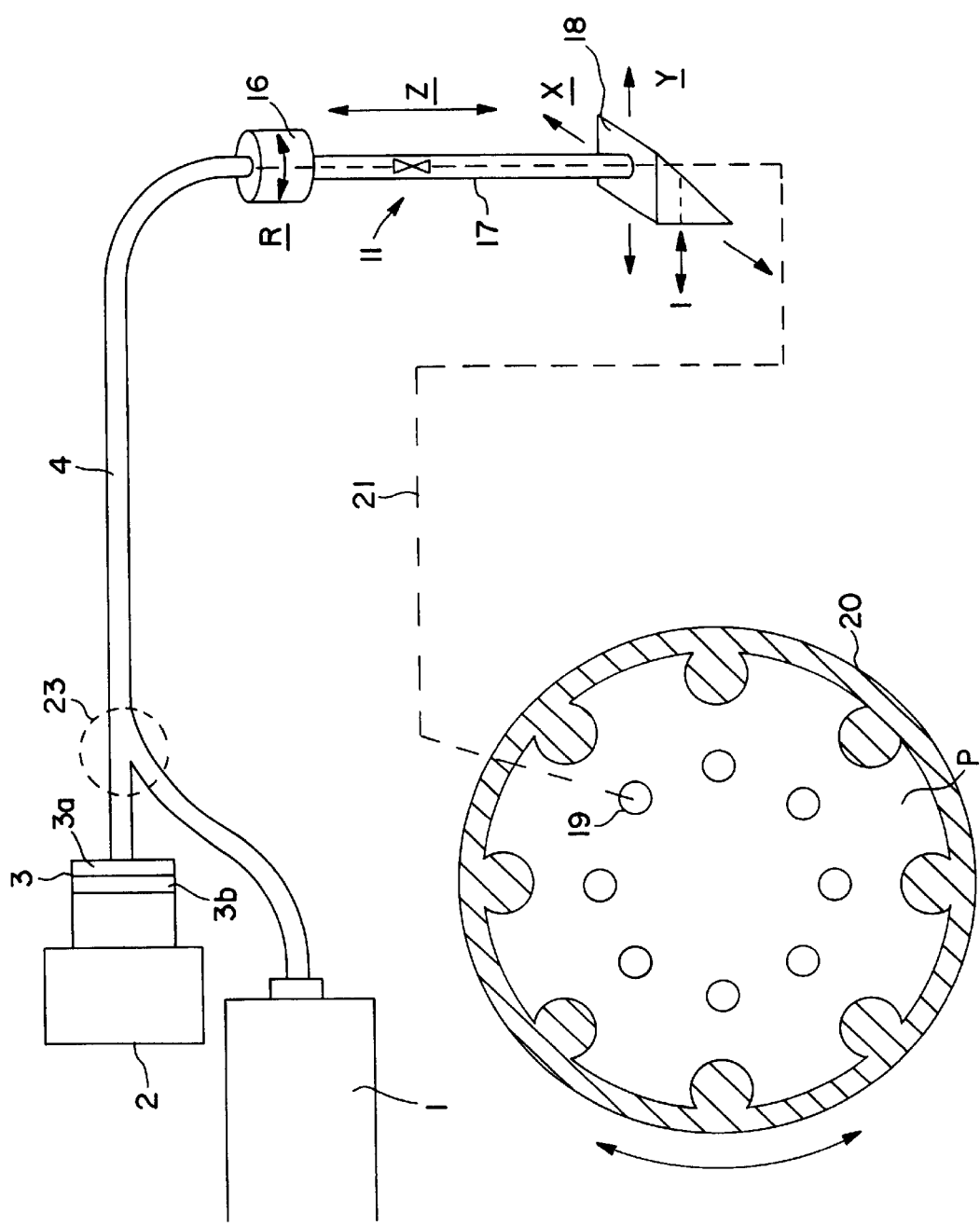
FIG. 4 is a diagram of a fourth embodiment using a dye penetration technique for examining bores or cells.
Figure 5:
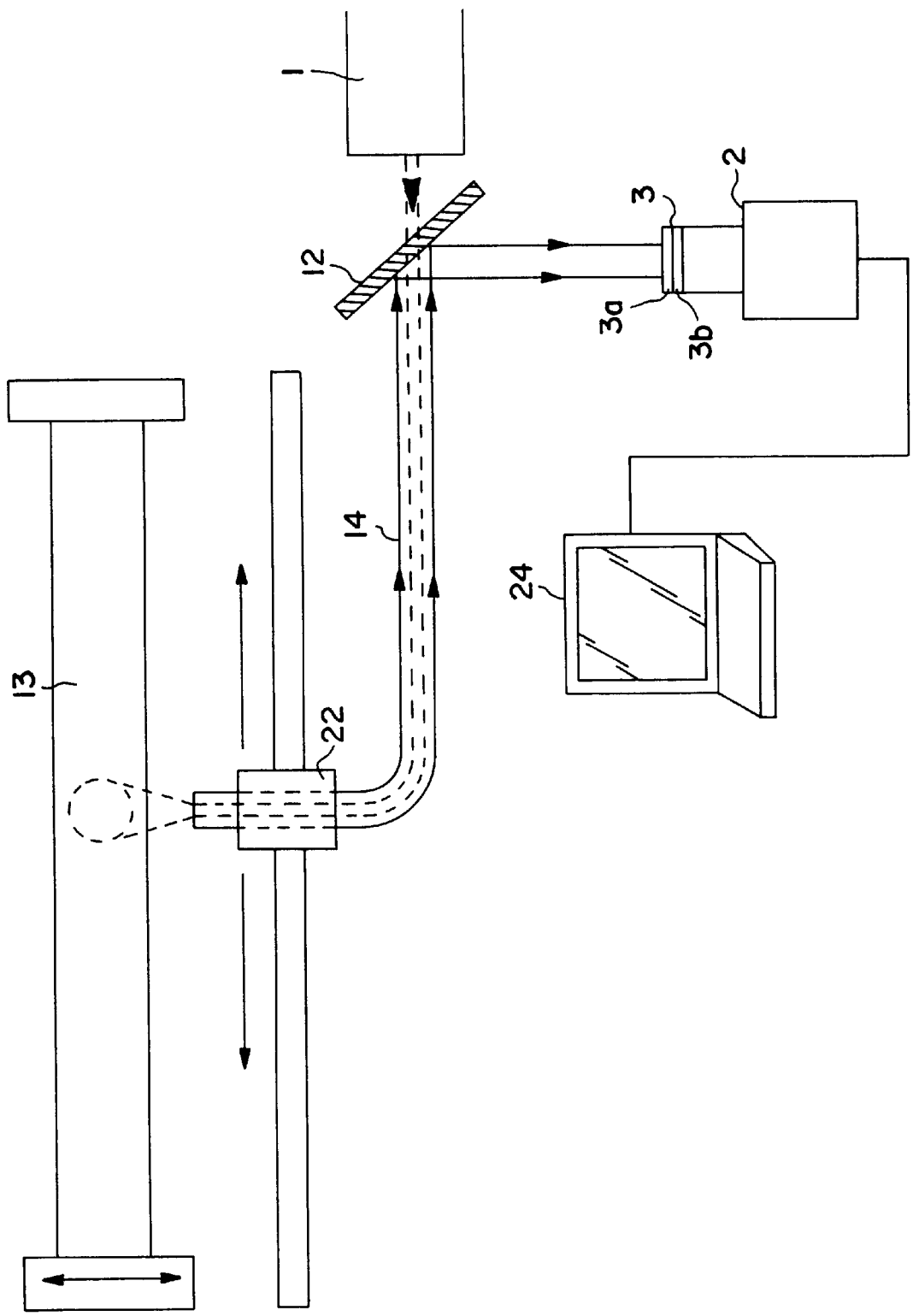
FIG. 5 is a diagram of a fifth embodiment applied to the magnetoscopic testing of bars.

The transmission (T) means can be of highly varied types:

in the FIG. 1 embodiment, the beam from the laser (1) is transmitted by optical fibers (4), the transmission means (T), to the surface (S) to be examined, in the FIG. 2 embodiment a plate (5) at the exit of the laser (1) splits the laser beam into a portion (6) which is conveyed by optical fibers or otherwise to a surface (7) of a part (8) to be observed and a portion (9) which is conveyed by optical fibers or otherwise to an opposite surface (10) of the part (8), in the FIG. 3 embodiment a plate (5) at the exit from the laser (1), as in the FIG. 2 embodiment, splits the beam from the laser into two beams (6, 9) which illuminate two respective faces (7) and (10) of a wall (8); in this example the system includes two sets of mirrors (M) and (MM) for transmitting the two beams to the surfaces (7, 10), in the FIG. 4 embodiment, the beam from the laser (1) is transmitted by optical fibers (4) to an endoscope (11) which enables the beam to reach areas to which access is difficult, for example to illuminate the internal surface of a bore or a cell, and in the FIG. 5 embodiment, the beam from the laser (1) passes through a plate (12) and is then conveyed to the surface to be examined, in this instance that of a bar (13), by optical fibers (14).

The above examples do not exclude other transmission means.

The incident laser beam is much narrower than the beam from a mercury vapor lamp or a neon tube. The invention therefore provides means for scanning the beam over the surface to be examined, either by moving the beam or by moving the surface.

In the FIG. 2 embodiment, the part (8) to be examined is placed on a turntable (15) which can be moved in translation along an axis (X) and which can move up and down along an axis (Z) parallel to the rotation axis of the part.

In the FIG. 3 embodiment, the mirrors for reflecting the two portions of the beams from the laser comprise, firstly, fixed mirrors (M1, M2) and, secondly, mirrors (MM1, MM2, MM3 and MM4) which can oscillate under the control of a computer programmed so that the beams scan the surfaces to be examined.

In the FIG. 4 embodiment, the endoscope includes a support 16 which can rotate about a rotation axis (R), a telescopic waveguide (17) along the rotation axis (Z) and an end prism (18) which can move along the (X, Y) axes, and the part (P) which includes the bores (19) to be examined is placed on a turntable (20). The line (21) in the figure symbolizes the fact that the end prism (18) can be lowered into the bore (19).

In the FIG. 5 embodiment, the part (13) observed is a bar which can rotate and the end of the fiber optic guide (14) is carried by a carriage (22) which can move parallel to the bar.

The observation video camera (2) and its polarized wave analyzer (3) are duplicated if it is necessary to observe two surfaces simultaneously, as is the case in FIGS. 2 and 3 embodiments.

Splitter plates are used, if required, to pass the incident rays and deflect the emergent rays (FIGS. 3 and 5).

In the FIG. 4 embodiment, an optical fiber coupler (23) is used to enable the same bundle of optical fibers (4) to transmit the incident beam from the laser (1) to the part (P) and to transmit the wave emitted by the excited dye to the video camera (2).

This is possible because the video camera used is not sensitive to ultraviolet radiation.

The equipment is calibrated using a block with cracks of known depth that has been prepared by dye penetration or magnetoscopy.

In the absence of the analyzer (3), or by locking the analyzer to the polarity of the laser (1), the image observed shows the presence of cracks in the block buried in light spots with the same wavelength caused by residual dye on the surface of the block.

If the analyzer according to the invention is rotated, the unwanted spots are seen to disappear progressively, leaving only the images due to the calibration cracks for one particular angle of rotation of the analyzer.

The analyzer is rotated further to examine the successive images of cracks in increasing depth order: it is therefore possible to draw up a calibration curve relating the angle of rotation of the analyzer to the depth of the cracks, enabling the depths of cracks in a surface examined to be determined subsequently.

A double analyzer is preferably used, i.e. an analyzer which includes two successive analyzers (3a, 3b), namely a front analyzer (3a) eliminating unwanted spots and a rear analyzer (3b) determining the depth of the cracks.

The two analyzers are mounted in a common turret, for example, and are rotated at the same time until the unwanted spots are eliminated, after which only one of the analyzers is rotated, to evaluate the depths of the cracks.

Each analyzer is of a type known in the art, for example a plate on one face of which are parallel lines of identical prisms.

The invention is not limited to the above embodiments.

What is claimed is:

1. A method of non-destructive testing of the state of a surface which may have cracks in it by observing waves emitted by a dye applied to the surface and present in the cracks in response to an incident excitation beam of wavelength appropriate to the dye, wherein the incident excitation beam is an ultraviolet light, wherein said beam is made of rectilinear polarized waves, wherein waves emitted by the dye are observed through a rotatable polarized wave analyzer, and wherein said analyzer is rotated first to eliminate from observation the wave due to the residual dye on the surface and thereafter to determine the depths of the cracks.

2. A method according to claim 1 wherein the said incident excitation beam is centered on a wavelength of 330 nanometers.

3. A method according to claim 1 or 2 wherein the waves emitted by the dye are observed by a camera which is not sensitive to ultraviolet radiation.

4. A method according to claim 1 or 2, which comprises a calibration process to establish angles of rotation of the analyzer which successively eliminate from observation cracks of increasing depth.

5. A method according to claim 1 or 2, wherein said surface is scanned with the incident beam by moving the surface or the incident beam during observation.

6. A system for implementing a dye penetration or magnetoscopic method using a dye applied to the surface and present in the cracks of a surface to be examined, which system includes:

production means for producing a polarized ultraviolet beam, transmission means for guiding that beam toward the surface to be examined, observation means of observing the waves emitted by the dye when excited by said beam, wherein said production means are selected to provide a rectilinear polarized ultraviolet beam, and wherein the system comprises a rotatable polarized wave analyzer on the path of the waves emitted by the dye between the surface and the observation means, whereby a rotation of the analyzer allows first to eliminate progressively from the observation the waves due to the residual dye on the surface and thereafter to determine the depth of the cracks.

7. A system according to claim 6, wherein the production means comprise a laser.

8. A system according to claim 6 or 7, wherein the ultraviolet beam is centered on a wavelength of 330 nanometers.

9. A system according to claim 6, wherein said observation means is a camera which is not sensitive to ultraviolet radiation.

10. A system according to claim 6 or 9, including means for moving the surface or the incident beam to scan the surface with the incident beam during observation.

11. A system according to claim 6 or 9, including oscillating mirrors controlled by computer to deflect the incident beam to cause it to scan the surface.

12. A device according to claim 6 or 9, wherein the transmission means include an endoscope terminating in a prism for entering a bore or a cell of a piece to be examined.

13. A system according to claim 6 or 9, wherein the angles of rotation of the analyzer have been calibrated corresponding to the depths of cracks.

14. A system according to claim 6 or 9, including two successive rotatable analyzers respectively for eliminating unwanted spots due to residual dye on the surface and for determining the depth of cracks.

* * * * *

UNITED STATES PATENT AND TRADEMARK OFFICE
CERTIFICATE OF CORRECTION

PATENT NO.    : 6,556,298 B1
DATED         : April 29, 2003
INVENTOR(S)   : Pailliotet Page 1 of 1

It is certified that error appears in the above-identified patent and that said Letters Patent is hereby corrected as shown below:

Title page,
Item [73], Assignee, please delete "Port St. Luae" and insert -- Port St. Lucie --.
Item [22], PCT Filed, please delete "Apr. 5, 1999" and insert -- August 5, 1999 --.

Signed and Sealed this

Seventeenth Day of August, 2004

JON W. DUDAS
*Acting Director of the United States Patent and Trademark Office*